(12) United States Patent
Brookfield

(10) Patent No.: US 9,243,882 B2
(45) Date of Patent: Jan. 26, 2016

(54) LOW FRICTION RHEOMETER

(75) Inventor: David A. Brookfield, Sharon, MA (US)

(73) Assignee: Brookfield Engineering Laboratories, Inc., Middleboro, MA (US)

(*) Notice: Subject to any disclaimer, the term of this patent is extended or adjusted under 35 U.S.C. 154(b) by 156 days.

(21) Appl. No.: 13/446,077

(22) Filed: Apr. 13, 2012

(65) Prior Publication Data

US 2012/0260723 A1   Oct. 18, 2012

Related U.S. Application Data

(60) Provisional application No. 61/476,062, filed on Apr. 15, 2011.

(51) Int. Cl.
*G01B 5/24* (2006.01)
*G01N 11/14* (2006.01)
(52) U.S. Cl.
CPC . *G01B 5/24* (2013.01); *G01N 11/14* (2013.01)
(58) Field of Classification Search
CPC .................................. G01B 5/24; G01N 11/14
USPC ............ 73/54.01, 54.02, 54.14, 54.28, 54.33, 73/54.37
See application file for complete search history.

(56) References Cited

U.S. PATENT DOCUMENTS

| | | | | |
|---|---|---|---|---|
| 3,722,262 A | * | 3/1973 | Gilinson et al. | 73/54.28 |
| 4,571,988 A | * | 2/1986 | Murphy, Jr. | 73/54.33 |
| 5,535,619 A | * | 7/1996 | Brookfield | 73/54.33 |
| 2002/0007666 A1 | * | 1/2002 | Robinson | 73/54.28 |
| 2002/0046597 A1 | * | 4/2002 | Brookfield | 73/54.28 |

* cited by examiner

*Primary Examiner* — Hezron E Williams
*Assistant Examiner* — Marrit Eyassu
(74) *Attorney, Agent, or Firm* — Burns & Levinson LLP; Jerry Cohen; David W. Gomes

(57) ABSTRACT

An improved rheometer and rotatable sensing shaft sub-assembly therefor with flexural pivot support at two ends of the shaft, and means for allowing limited axial movement of the shaft while maintaining rigid radial support, with transducer means for extracting and signaling rotational position of the shaft based on shear stress of a fluent material contacting a spindle, cone/plate or other extension of the shaft and/or a related motor-driven member such as a cylinder.

4 Claims, 2 Drawing Sheets

LOW FRICTION RHEOMETER

CROSS-REFERENCE TO RELATED APPLICATIONS

Priority is claimed from Applicant's provisional U.S. application Ser. No. 61/476,062 filed Apr. 15, 2011. The full content of said application is incorporated herein by reference as though set out herein.

FIELD AND BACKGROUND OF THE INVENTION

The present invention relates to rheometer instruments and similar apparatus for measuring visco-elastic properties of fluent materials (e.g. viscometers), such as liquids, gels, slurries, powder masses, plastics, elastomers, clays, foodstuffs and the like, and more particularly to enabling a new paradigm of the field of achieving low friction and high sensitivity without a complex or expensive apparatus arrangement. The sensing shaft control sub-assembly of the invention is also useful for shaft elements of other kinds including, e.g. probes, rotors or float parts, delicate medical and scientific instruments.

Rheometers measure flows of fluent materials (liquids, slurries, suspensions, elastomers, plastics, gels, melts, (powdery masses), plastics, elastomers, clays, foodstuffs and the like where adequate characterization demands more than a viscosity measurement that can be made by a viscometer. The field of rheometers includes instruments using well known per se rotational cylinders and cone-plate devices contacting the materials to be measured and other forms (e.g. extrusional and capillary forms).

State of the art is summarized and advanced in U.S. Pat. No. 7,207,210 of D. J. Moonay and U.S. Pat. Nos. 5,167,143 and 4,175,425 (all of common assignment with the present application) and references cited therein, all incorporated herein by reference as though set out at length herein.

SUMMARY OF THE INVENTION

The present invention (which can be applied to rotational cylinder, cone and plates and other arrangements for interaction with materials) provides a driver element and a sensing element, usually a shaft, the latter supported by flexural (flex) pivots and operating on a small angle (hereinafter defined) to afford essentially frictionless operation, high signal to noise ratio and high sensitivity, while enabling a simple, low cost arrangement which allows movement axially and rotationally but is rigid radially. Readout of sensing shaft axial or rotary A deflection can be made by magnetic, field effect, electrostatic strain gage or other means, but preferably is done for rotation with a microsyn transducer with field coils and a rotor. Stop means are provided to limit sensing shaft axial and rotary deflection based on shear response range of interest of the material being measured and protection of the flexing elements.

Other objects, features and advantages will be apparent from the following detailed description of preferred embodiments taken in conjunction with the accompanying drawings in which:

BRIEF DESCRIPTION OF PREFERRED EMBODIMENTS

Referring to FIGS. 1-5, there is shown a housing H, a rotary motor M, a wheel DR1 driven by the motor and in turn driving a belt B to drive a wheel DR2. The driver wheel DR2 supports, via an attachment member AM, a cone-plate, rotational cylinder or spindle rod or other measured material contact member (not shown).

Figure 1:
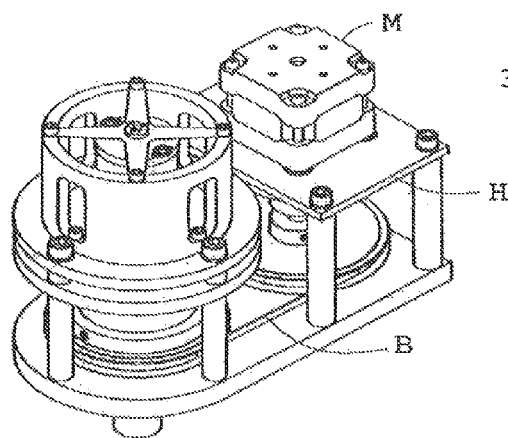
FIG. 1 is an isometric view of a rheometer instrument made in accordance with a preferred embodiment of the present invention.
Figure 2:
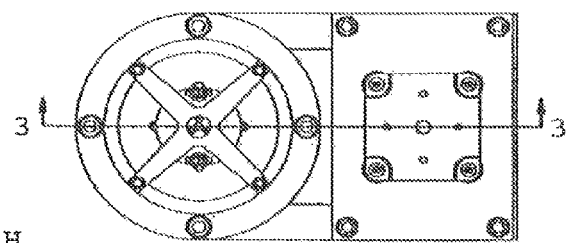
FIG. 2 is a top view of it and FIG. 4 a side view.
Figure 3:
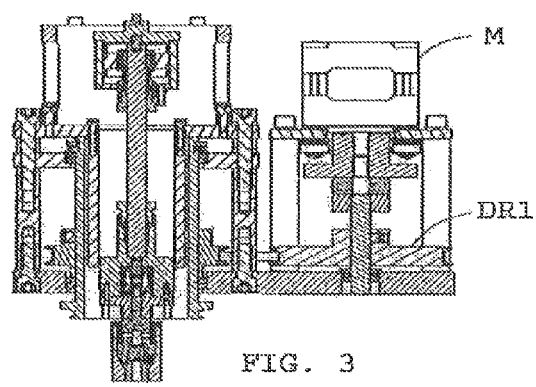
FIG. 3 is a cross sectional view of it taken as indicated at A-A in FIG. 2.
Figure 5:
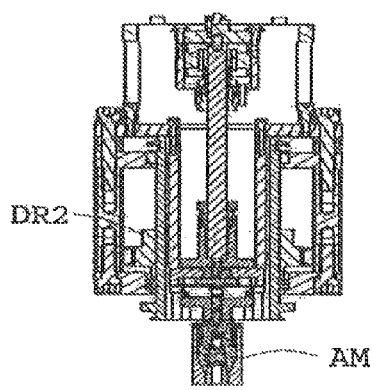
FIG. 5 is a cross sectional view of it taken as indicated at B-B in FIG. 4.
Figure 4:
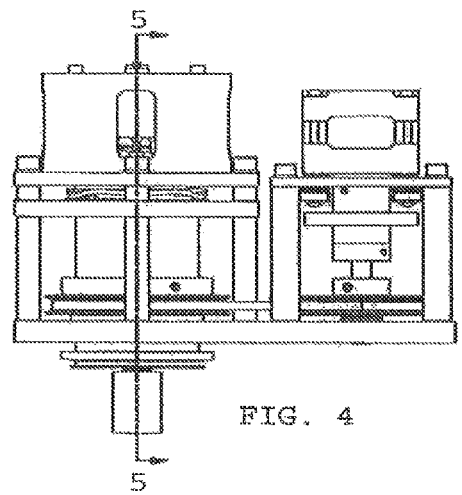
Figure 6:
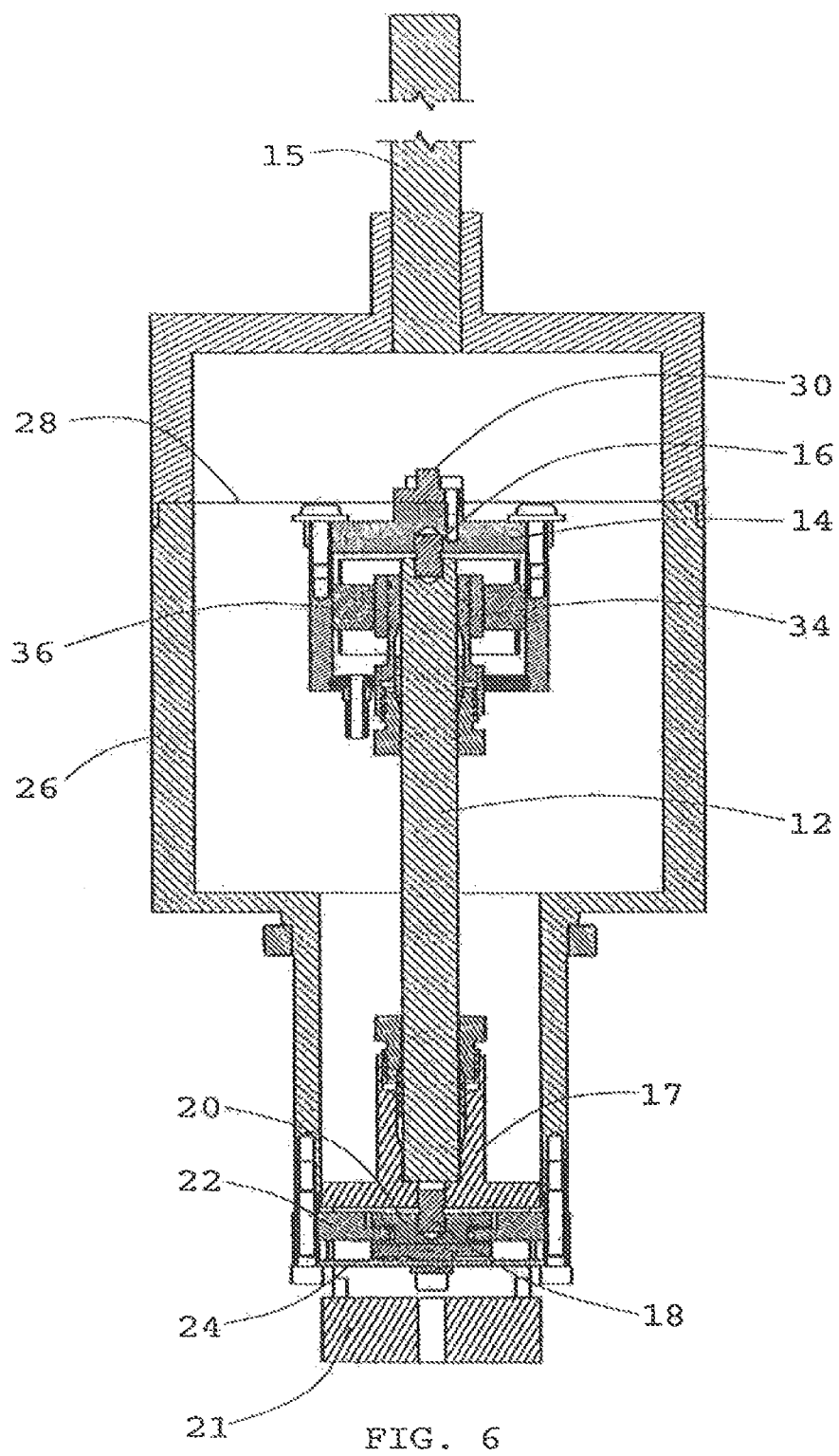
FIG. 6 is an enlarged view of its internal structure.

As shown in FIG. 6 sensing shaft 12 is provided that is attached at its upper end from an upper pivot support 14 by an upper flex pivot 16 and at the lower end to a lower sensing block 17 via a lower flex pivot 18. FIG. 6, element 15 is the shaft extension of the motion. The lower flex pivot is also attached to a flex pivot axial limiter 20 which provides a limited movement of the sensing shaft in the axial direction due to engagement of the limiter with a stop bracket 22. The axial limiter is clamped to a lower flexing element 24 which provides rigid radial support while allowing for limited axial movement. FIG. 6, element 21 refers to the conventional holder of the fluent material contact means, e.g., a cone of a cone-plate viscometer or a cylinder immersed in the fluent material. The lower flexing element is clamped to cylinder 26 and therefore controls the positioning of the lower flex pivot, which in turn controls the positioning of the lower sensing block. The radial clearance between the lower sensing block and the cylinder is kept small to prevent excessive radial movement which would damage the lower flex pivot.

The upper flex pivot is attached to the upper flex pivot support, which is further clamped to the upper flexing element 28 by axial clamp 30. As with the lower flexing element this allows some axial movement of the sensing shaft but is rigid for radial movement, The upper flexing element is clamped to cylinder 26 to complete the suspension system for the sensing shaft. A microsyn transducer system with a rotor 34 and field coil 36 is provided at the upper end of the sensing pivot. In order to assure alignment between the transducer components, especially as the sensing shaft moves axially, the microsyn rotor is clamped to the sensing shaft near the upper flex pivot support, while the microsyn field coil 36 is mounted directly to the upper flex pivot support thereby allowing no relative axial movement between the transducer field and rotor.

The above described arrangement allows axial movement of the sensing shaft within the limits defined by the stop bracket 22, and permits rotational movement of the sensing shaft through the flex pivots. The rotation of the flex pivots has to be limited to a small angle, so the clearance between the lower sensing block and the stop bracket in the rotational sense is established such that at an acceptable angle of rotation the two parts will engage in either direction and not permit further rotation. The amount of axial movement allowed is determined by the amount of movement necessary for full scale deflection of an appropriate load cell or other similar arrangements or device attached to the axial clamp for the purpose of measuring normal forces and to determine the hit point when using cone and plate geometry for establishing a known gap. Rotation of the sensing system against a stationary member or keeping the sensing system stationary and rotating the complementary member or even rotating both parts simultaneously are all feasible variants and desirable.

The limited rotation, axial movement, limited sensing sub-assembly of the present invention can be used in several contexts additionally to its presently described uses in rheometors (and viscometers). Single or multiple ranges of measured rotation calibration can be provided (e.g. to handle measurement of a fluid over single or multiple ranges of viscosity or shear stress charge). Some of the other applications include fine control and detection of positions of probe ends or other parts (e.g. rotors or float parts) of scientific and medical instruments, motors and the like.

it will now be apparent to those skilled in the art that other embodiments. improvements, details, and uses can be made consistent with the letter and spirit of the foregoing disclosure and within the scope of this patent, which is limited only by the following claims. construed in accordance with the patent law, including the doctrine of equivalents.

The invention claimed is:

1. A limited rotation sensing assembly usable in combination, with a fluent material (liquids, gels, slurries, powder masses, plastics, elastomers, clays or foodstuffs) contact means to perform rheometry and/or viscometry functions; and comprising, in combination:
   (a) a sensing shaft connected to the fluent material contact means and itself suspended by flexural pivots at two points separated along the length of the shaft to ensure alignment,
   (b) a support structure, for the shaft with upper and lower support elements
   (c) means connected to the support structure for holding each flexural pivot in a manner to fix its lateral position but allowing limited rotational movement of the sensing shaft pivots and limited axial movement of said pivots,
   (d) stop means for limiting such axial and rotational movements to define a measurement range, and
   (e) a transducer with components engaged with the sensing shaft to detect and signal its rotary motion, the transducer having a rotor shaft, component of the transducer clamped to the sensing shaft at the upper flexure pivot location and a stator clamped directly to the support means for the upper flexural pivot, with stop means at the flexure pivot location limiting axial movement of the sensing and
   (f) the stop means allowing movement of each flexural pivot clockwise and counterclockwise with limits of flexural rotation to cover transducer full scale and in limiting axial movement, without any reactive movement of rotor and stator portions of the transducer.

2. The sensing assembly of claim 1 configured as a rheometer implementing shear stress measurements.

3. The apparatus of claim 2 and further comprising means for indicating limit of a range of allowed axial movement.

4. The apparatus of any one claims 1-3 wherein the transducer is a microsyn transducer.

* * * * *